United States Patent
Dimitrov

(10) Patent No.: US 11,071,798 B2
(45) Date of Patent: Jul. 27, 2021

(54) CURATIVE CAPSULE

(71) Applicant: Dimitar Stoev Dimitrov, Sofia (BG)

(72) Inventor: Dimitar Stoev Dimitrov, Sofia (BG)

(*) Notice: Subject to any disclaimer, the term of this patent is extended or adjusted under 35 U.S.C. 154(b) by 103 days.

(21) Appl. No.: 16/704,703

(22) Filed: Dec. 5, 2019

(65) Prior Publication Data

US 2021/0170059 A1   Jun. 10, 2021

(51) Int. Cl.
*A61L 2/10* (2006.01)
*A61K 9/48* (2006.01)

(52) U.S. Cl.
CPC .............. *A61L 2/10* (2013.01); *A61K 9/4825* (2013.01)

(58) Field of Classification Search
CPC ................................ A61L 2/10; A61K 9/4825
See application file for complete search history.

(56) References Cited

U.S. PATENT DOCUMENTS

| | | | |
|---|---|---|---|
| 2007/0010859 A1* | 1/2007 | DiMauro | A61N 5/0603 607/94 |
| 2009/0118583 A1* | 5/2009 | Matsumoto | A61B 1/041 600/118 |
| 2016/0263261 A1* | 9/2016 | Trapani | A61L 2/10 |
| 2017/0014056 A1* | 1/2017 | Newberry | A61B 5/1455 |

* cited by examiner

*Primary Examiner* — Sean M Luck

(57) ABSTRACT

An ingestible capsule is provided. The capsule comprises a shell container containing an ultraviolet emitter, and an energy source connected to the emitter. The capsule also comprises a gelatinous layer encasing the shell container. After ingestion, ultraviolet rays emitted by the emitter reach gastric areas hosting bacteria afflicting an ingesting user, the rays at least partially eradicating the bacteria.

20 Claims, 1 Drawing Sheet

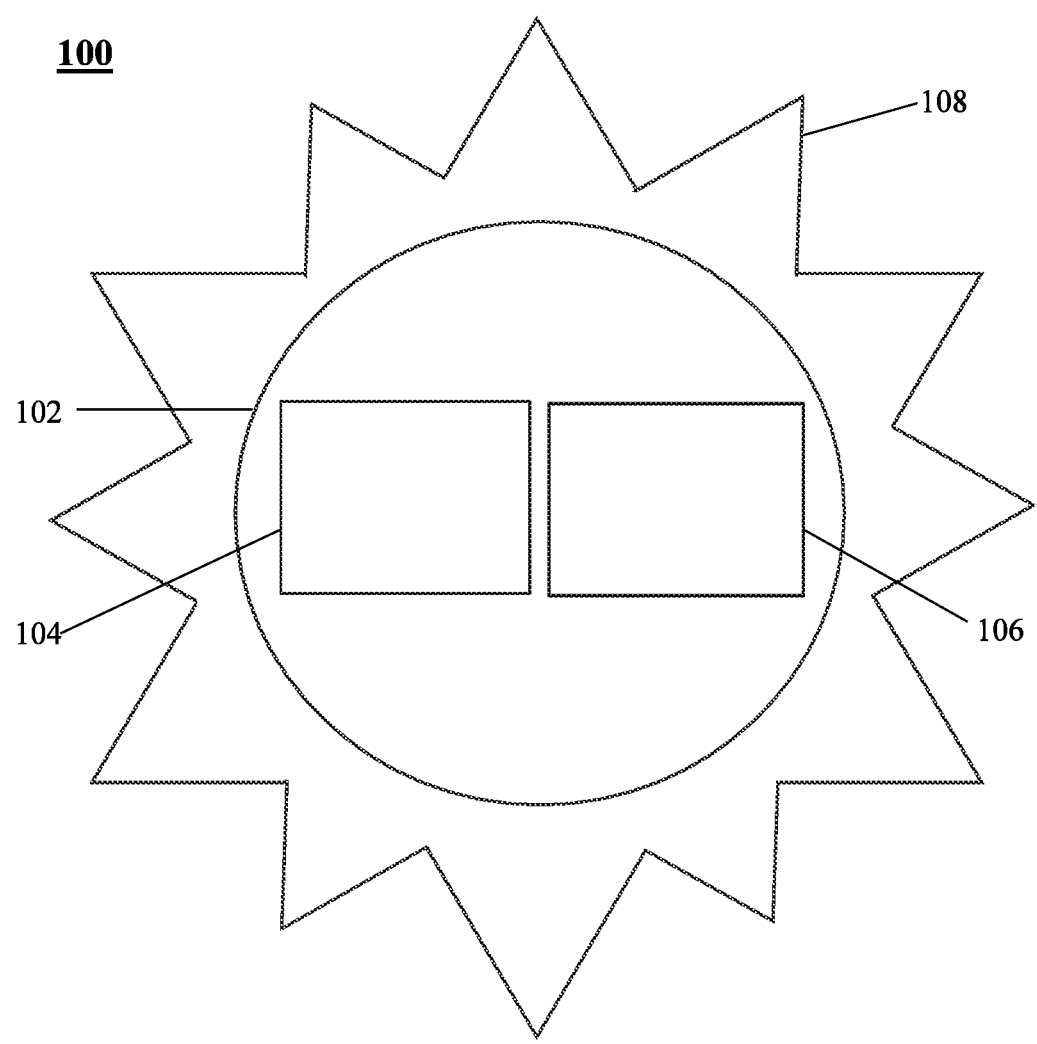

CURATIVE CAPSULE

FIELD OF THE INVENTION

The present disclosure is in the field of health care. More particularly, the present disclosure provides a curative capsule that upon ingestion provides energy to an emitter that projects ultraviolet rays to areas of the stomach afflicted with harmful bacteria.

BACKGROUND

*Helicobacter pylori* (*H. pylori*) is a bacterium that causes chronic gastritis, ulcers, and gastric cancer. More than half of the global population may suffer from *H. pylori*, mostly in developing countries. *H. pylori* may spread via contaminated water and food.

Various combinations of antibiotics may be used to eradicate *H. pylori* but serious side effects may result. Such combinations are expensive and therefore beyond the reach of most afflicted persons. Further, some strains of *H. pylori* are resistant to medications.

*Helicobacter pylori* is sensitive to ultraviolet (UV) light. The bacteria may perish rapidly when treated with such light.

Previous implementations have attempted to treat *Helicobacter pylori*. In one implementation, a device is described by a German publication designated DE102010010763A1. The device consists of a probe, an outer tube of which is inserted into a patient's esophagus. Two smaller tubes are placed inside the outer tube. A first of the two smaller tubes receives placement of a fiber bundle conducting UV radiation to the stomach, the UV radiation received from a source external to the patient's body.

A second of the two smaller tubes is connected to a source for fluid delivery, the fluid comprising a water solution or air. The fluid is heated to 37 degrees Fahrenheit. This temperature is measured by a sensor mounted on an outer surface of the outer tube. Before beginning conduction of the UV radiation, a stopper is inserted into the patient's stomach and located on the pillory.

An aim of introducing the fluid as provided by publication DE102010010763A1 is to inflate the stomach and cause the epithelium fringes to open and promote the UV radiation to receive unobstructed access to each fold of the stomach. During this stage of the treatment, the patient is lying down on a table mounted on an axis which may allow periodical inclination of the patient's body Use of such probe as provided by publication DE102010010763A1 may cause discomfort for the patient. The manipulation with the probe is therefore performed after the patient is placed under anesthesia. After this procedure, the patient must be hospitalized.

Manipulation as provided by publication DE102010010763A1 is expensive and time consuming and requires specialized equipment and a highly trained team of specialists. Further, the probe must be cleaned after every intervention to address the risk of transmitting the bacteria to subsequent patients.

BRIEF DESCRIPTION OF THE DRAWING

FIG. 1 is a diagram of a system of a curative capsule according to an embodiment of the present disclosure.

SUMMARY

A curative capsule is provided for single use to achieve a painless eradication of *H. pylori* from a patient's stomach. Systems and methods provided herein avoid the use of specialized equipment and specialized personnel without causing discomfort to the patient.

The curative capsule contains a source of energy connected to a UV emitter. The energy source and emitter are connected and placed within a shell of the capsule. The shell is made of material permeable by UV radiation and is insoluble in gastric juices.

The shell is encapsulated in a clear gelatinous layer. The outer surface of the layer is rugged with a plurality of conical sections.

The treatment provided herein is painless and obviates a need for sedation, specialized equipment, and specialized personnel. The treatment may be administered in the patient's home. The capsule is for single use by one patient. The treatment may be less expensive than others and therefore accessible to a wide range of patients.

DETAILED DESCRIPTION OF THE INVENTION

FIG. 1 is a diagram of a system of a curative capsule according to an embodiment of the present disclosure. FIG. 1 depicts components and interactions of a curative capsule system 100.

The curative capsule system 100 comprises a shell container 102, a power source 104, a UV emitter 106, and a gelatinous layer 108. The shell container 102, the UV emitter 106 and the gelatinous layer 108 may be referred to for brevity purposes as the shell 102, the emitter 106 and the layer 108, respectively.

The shell 102 is made of a material that is permeable by UV radiation. The shell 102 is insoluble in gastric juices and other liquids, and food and non-food substances that may be resident in a patient's stomach.

The power source 104 and the emitter 106 are contained within the shell 102 and connected to each other. The power source 104 provides power to the emitter 106.

The shell 102 is encased within the layer 108 which is also permeable by UV radiation. The presence of the layer 108 around the shell 102 results in the overall system 100 to be large enough that it cannot pass through the pylorus of the patient when the system 100 is initially ingested.

The layer 108 is shaped with conical sections or horns that protrude outward. After ingestion and as the capsule 100 moves within the patient's stomach, the conical sections or horns penetrate the epithelium fringes of the stomach. The power source 104 feeds power to the emitter 106. The emitter 106, based on receiving the power, emits UV radiation. Because the epithelium fringes have been penetrated, the UV radiation makes contact with and is able to at least partially eradicate *H. pylori* bacteria in the patient's stomach, providing relief to the patient.

The curative capsule 100 when is ingested is about 12 millimeters in diameter and therefore cannot pass through the pylorus of the patient. After about thirty minutes in the patient's stomach the layer 108 is fully disintegrated and the remaining shell 102 is about 6 millimeters in diameter. At such a diameter, the shell 102 passes gently through the pylorus and is eventually voided normally by the patient.

Thirty minutes is also about the useful life of the power source 104. Therefore, the power source 104 is exhausted about the same time that the layer 108 is fully disintegrated. As such, the capsule 100 passes from the patient's gastrointestinal tract at about the time the power source 104 expires and the emitter 106 finishes transmitting UV radiation. The therapeutic treatment ends and the shell 102 begins its movement from the patient's body. The *H. pylori* bacteria may be at least partially eradicated from the patient's body and the patient may consequently experience relief. In other embodiments, systems and methods provided herein may be used to treat afflictions other than *H. pylori*.

What is claimed is:

1. An ingestible capsule, comprising:
   a shell container containing:
      an ultraviolet emitter, and
      an energy source connected to the emitter,
   a gelatinous layer encasing the shell container
   wherein after ingestion, ultraviolet rays emitted by the emitter reach gastric areas hosting bacteria afflicting an ingesting user, the rays at least partially eradicating the bacteria.

2. The system of claim 1, wherein upon ingestion, the capsule with gelatinous layer is about 12 millimeters in diameter and cannot pass through a pylorus of an ingesting user.

3. The system of claim 1, wherein about thirty minutes after ingestion, the layer is dissolved.

4. The system of claim 3, wherein after dissolution of the layer, the capsule is about 6 millimeters in diameter and passes through the pylorus.

5. The system of claim 1, wherein about thirty minutes after ingestion, the energy source exhausts and the emitter ceases functioning.

6. The system of claim 1, wherein the gelatinous layer features conical sections.

7. The system of claim 6, wherein the conical sections penetrate between epithelium fringes.

8. The system of claim 1, wherein the shell container is made of material that is permeable by ultraviolet radiation and is further insoluble in gastric juices, in food substances, and in non-food substances in the gastric areas.

9. A method for treating *Helicobacter pylori* bacteria resident in a human stomach, comprising:
   a capsule receiving ingestion into a stomach of a user;
   the capsule, via a gelatinous outer layer of the capsule, penetrating between epithelium fringes of the stomach;
   the capsule emitting ultraviolet rays to areas of the stomach afflicted by *Helicobacter pylori* bacteria; and
   the capsule, after the gelatinous layer has dissolved, passing through a pylorus of the user.

10. The method of claim 9, further comprising an energy source situated within a shell container of the capsule providing energy to an ultraviolet emitter also inside the shell container.

11. The method of claim 9, further comprising the capsule and the gelatinous layer measuring about 12 millimeters in diameter upon ingestion.

12. The method of claim 11, further comprising the capsule with layer at the 12 millimeter diameter not passing through a pylorus of the user after ingestion.

13. The method of claim 9, further comprising the gelatinous layer dissolving about thirty minutes after ingestion.

14. The method of claim 13, wherein after dissolution of the layer, the capsule is about 6 millimeters in diameter and passes through the pylorus.

15. A system for treatment for removing *Helicobacter pylori* bacteria from the stomach, comprising:
   an ultraviolet emitter;
   a miniature battery configured to provide energy to the emitter;
   a shell containing the emitter and the battery; and
   a gelatinous layer encasing the shell,
   wherein after ingestion of the shell and layer, the emitter, based on receipt of the energy, emits ultraviolet rays to at least partially remove *Helicobacter pylori* bacteria from the stomach.

16. The system of claim 15, wherein the shell is made of material that is permeable by the ultraviolet rays.

17. The system of claim 15, wherein the layer has conical sections promoting penetration of epithelium fringes.

18. The system of claim 15, wherein the layer dissolves about thirty minutes after ingestion.

19. The system of claim 18, wherein after dissolution of the layer the shell passes through the pylorus.

20. The system of claim 15, wherein the battery is exhausted about thirty minutes after ingestion.

* * * * *